(12) United States Patent
Prisell

(10) Patent No.: US 6,626,865 B1
(45) Date of Patent: Sep. 30, 2003

(54) METHOD AND A DEVICE FOR MARKING SURFACES

(75) Inventor: Per Prisell, Stockholm (SE)

(73) Assignee: P Prisell AB, Stockholm (SE)

( * ) Notice: Subject to any disclaimer, the term of this patent is extended or adjusted under 35 U.S.C. 154(b) by 0 days.

(21) Appl. No.: 09/830,190

(22) PCT Filed: Oct. 25, 1999

(86) PCT No.: PCT/SE99/01924

§ 371 (c)(1),
(2), (4) Date: Apr. 23, 2001

(87) PCT Pub. No.: WO00/24323

PCT Pub. Date: May 4, 2000

(30) Foreign Application Priority Data

Oct. 23, 1998 (SE) ................................. 9803647

(51) Int. Cl.$^7$ ................................. A61B 10/00
(52) U.S. Cl. ........................................ 604/116; 606/131
(58) Field of Search ................ 606/131, 132, 606/167, 184; 604/115, 116, 117; 600/564, 567

(56) References Cited

U.S. PATENT DOCUMENTS

| | | | | |
|---|---|---|---|---|
| 3,522,800 A | * | 8/1970 | Lesser | 128/20 |
| 4,192,312 A | * | 3/1980 | Wilson | 128/853 |
| 4,279,259 A | * | 7/1981 | Lee et al. | 33/512 |
| 4,542,742 A | * | 9/1985 | Winkelman et al. | 606/167 |
| 4,576,163 A | * | 3/1986 | Bliss | 606/1 |
| 4,944,737 A | * | 7/1990 | Bloom | 128/898 |
| 5,123,907 A | * | 6/1992 | Romaine | 604/115 |

FOREIGN PATENT DOCUMENTS

EP          331392 A2 * 9/1989 ........... A61L/15/03

* cited by examiner

Primary Examiner—Danny Worrell
(74) Attorney, Agent, or Firm—Browdy and Neimark, P.L.L.C.

(57) ABSTRACT

A method for indicating the periphery line of a patch of an optionally resilient surface layer of a substrate object which patch is intended to be removed in a step, which may cause a change of the appearance of the surface, which method comprises the application on the surface of an adhesive mask, comprising an outer, "negative: and/or optionally an inner, slat "positive" mask component, comprising one or more layers of a sheet material, which can be brought to adhere to the surface of the object, wherein the negative mask comprises a main opening with a borderline, which forms an inner borderline of the mask, and the positive mask comprises a slab with a borderline, which forms an outer borderline of the mask, said inner and/or outer borderlines having essentially the shape of the intended periphery line of the patch of the surface layer intended to be removed, said main opening of slab having circular or preferably elongated, non-circular shape, preferably with a ratio of lengthwise extension on transverse extension of at least 2 or at least 3 and optionally at most 10.

12 Claims, 8 Drawing Sheets

METHOD AND A DEVICE FOR MARKING SURFACES

This invention can be used in a method mediating a safe and an optimal cosmetic and functional end result for removing; excise, skin, e.g. skin pathologies, e.g. skin tumors, cosmetically improper skin defects/findings or excessive skin. This invention is related to a method for indicating a periphery line, forming at least a part of a loop on a part of a surface area, in the following denoted "patch", especially a patch of an optionally resilient surface layer of a substrate object, which patch is intended to be removed in a step, which may cause a change of the appearance of the surface. This method is especially suited for indicating a periphery line on the skin of an animal, such as a mammal, e.g. a human.

It is previously known how to remove parts of a resilient surface layer, e.g. a patch of the skin of a human, with a cutting tool like a surgical scalpel or with a cutting edged tool, such as a punch provided with a number of V-shaped cutting blades, or a punch of circular shape. Such instruments and methods are disclosed e.g. in U.S. Pat. Nos. 5,123,907, 4,192,312 4,576,163, 4,832,045 and 4,542,742. Such cutting instruments are applied substantially on free hand until the desired depth of the cut is reached. When treating malignant skin tumors there is an obvious lack of safety when using a punch without a guiding means since the area of interest is covered by the punch itself during the actual cutting maneuver and thereby it is virtually impossible to verify that there are free macroscopic cutting margins to the tumor. The use of larger circular punches is furthermore restricted, since it is difficult or impossible to close the resulting skin defect in a cosmetically and functionally acceptable way, by a stitching operation.

The method according to this invention comprises the application on the surface of the object of a device, in the following denoted a "mask", preferably sterile, which may comprise a "negative" mask comprising a hole with a borderline having essentially the shape of the desired periphery line, and/or a "positive" mask, in the following also denoted a "slab", which comprises a piece of material with an outer borderline having essentially the shape of the desired periphery line. In a combined "negative" and "positive" mask the positive mask or slab essentially fills the hole in the negative mask, e.g. leaving a narrow uncovered area of preferably uniform width between said two masks. The negative and positive masks are in the following exemplified with a piece of sheet-shaped material, e.g. comprising one or more layers of sheet materials, preferably with adhesive characteristics, provided e.g. by an adhesive coating, which makes the mask adhere to the surface of the object. A negative mask according to this invention, when applied on the surface of the object, comprises a main opening with a borderline, also called inner borderline of the mask, which has essentially the shape of the periphery line of the patch, which should be indicated on the surface and optionally removed. Optionally a sterile non-sticky mask, used in combination with a sterile marking pen, can function as a "secondary template", thereby marking the patch/area of interest and removed prior to the cutting/punching procedure. In the text, the expression "mask" thereby also includes the secondary template.

In order to choose a safe and optimal size and form of planned skin excision a preferably non-sterile template (in the following also denoted mould or model) for simulating the periphery line of the patch on the substrate is included in the invention.

The templates and masks are preferably of a non-hemostatic type, i.e. not intended to be pressed into the skin for restricting the flow of blood in the skin area and neither for the forming of a temporary pressure mark in the skin.

The invention also includes a cutting tool/punch having the corresponding size and form to each chosen variant of mask and template.

The invention comprises a kit of two or three of the following components 1, 2 and 3; 1) one or more masks, 2) one or more cutting or punching tools that can be guided by the corresponding mask, and 3) a template device for simulating a periphery line on a substrate indicating what size and shape of mask and corresponding cutting tool should be chosen.

The invention thus includes a safe novel method where the area intended to be removed before surgery could clearly be inspected and controlled for e.g. satisfying free margins, alignment with skin wrinkles etc. and that the following surgical procedure is mechanically guided by a device; the mask (or marking).

The invention is in following mainly illustrated with reference to negative masks, but that which is said about negative masks essentially applies also to positive masks or combinations of negative/positive masks, e.g. as regards shape, materials, etc.

The enclosed drawings show presently preferred embodiments of the invention but are only intended for illustrating the invention without any restrictions thereof. The figures of the drawings show the following:

FIG. 1 shows a mask 4a of an adhesive sheet material, with a larger, elongated main opening 7, the periphery of which forms a borderline 5a. Adjacent to the borderline is an array of secondary minor openings 6, through which the point of a marking pen can be inserted. The minor openings 6 are evenly distributed; e and evenly positioned; d, from the opening 7.

FIG. 2 shows the mask of FIG. 1 in a perspective view.

FIG. 3 and FIG. 4 show a cutting tool with a handle 8, e.g. of plastics, and a cutting blade with a height "h" and a cutting edge 9 fastened to said handle, having an elongated cutting blade, as seen on FIG. 4, exemplified by an oval shape with a lengthways extension c and a transverse extension a. The cutting edge is shaped essentially to lie in a flat plane indicated with a broken line 24.

FIG. 4 shows the tool according to FIG. 3 seen from below.

FIG. 5 shows the (negative) mask 4a and the cutting tool 8, 9 of FIG. 3, 4 applied to a substrate layer 3, such as the skin of a mammal.

FIG. 6 shows die arrangement of FIG. 5 after cutting through the substrate layer 3 and removal of the cutting tool 8,9, and indicates with an arrow the removal of a patch 2 of the substrate layer with the periphery line 1 indicating the border of the cut-out patch 2 and of the opening formed in the substrate layer 3 by said cut-out. Indicated on the patch 2 is a pathological finding 13, which is desired to be kept intact and completely to be removed from the substrate together with the patch.

FIG. 7 shows a mould or template means, 10, exemplifying simulating periphery lines. The simulating means is a set of openings 11, of mutually varying size and/or shape and with borderlines 12 for simulating the desired periphery lines. Each opening size and shape has its corresponding mask and corresponding cutting tool.

Figure 11:
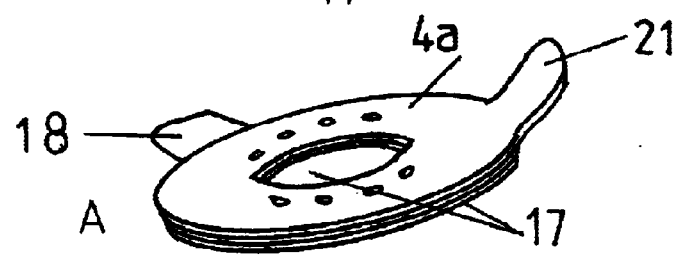
Figure 11:
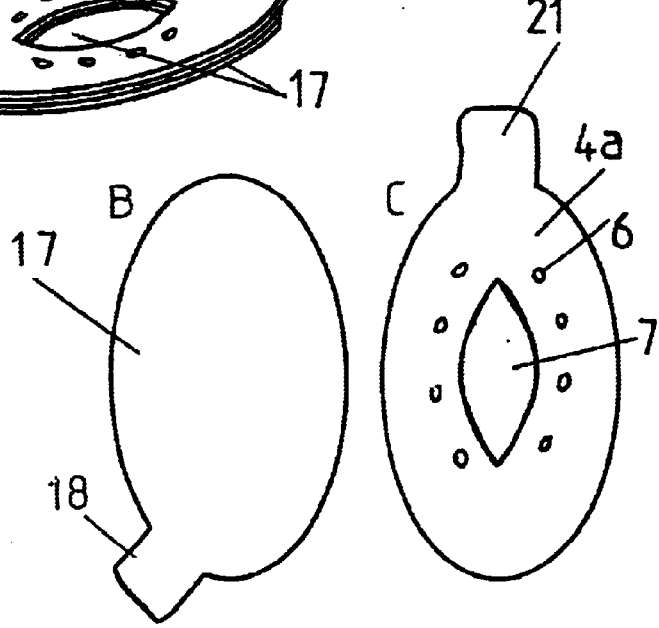

FIGS. 11; A, B, C and 12 show a mask with a lower protective layer 17. The adhesive material 22 is protected by the lower layer 17, which extend beyond the intermediate mask sheet material 4a as a gripping tab; 18. In order to facilitate the complete removal of the mask, 4a, a non-adhesive gripping tab; 21 is connected to the mask.

Figure 12:
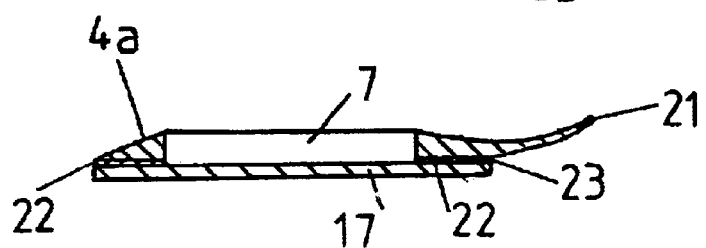

FIG. 12 shows a cross section through the mask assembly according to FIG. 11. The outer borderline 23 of the adhesive part 22 is shown under the tab 21.

Figure 13:
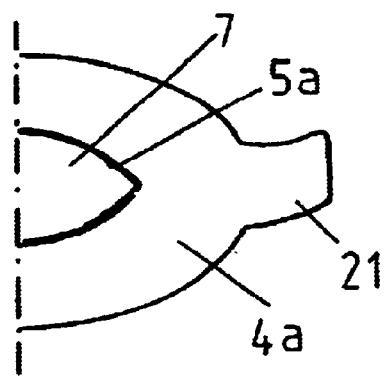

FIG. 13 is a view from above of a part of a mask of this invention with the gripping tab 21.

Figure 14:
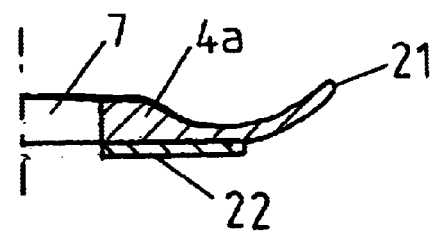

FIG. 14 is a cross section of the mask of FIG. 13 showing an adhesive layer 22 and a cross section thickness of the mask increasing from the outer border towards the inner border 5a.

Figure 15:
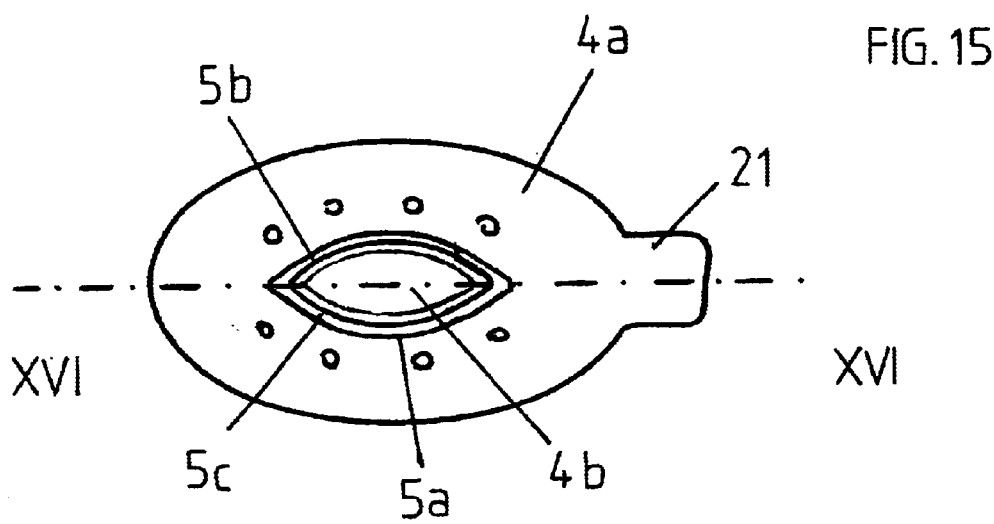

FIG. 15 shows a view from above of an optional combination of the positive 4b and negative 4a mask, wherein a boundary area in the shape of a gap 5c is present between the two mask components.

Figure 16:
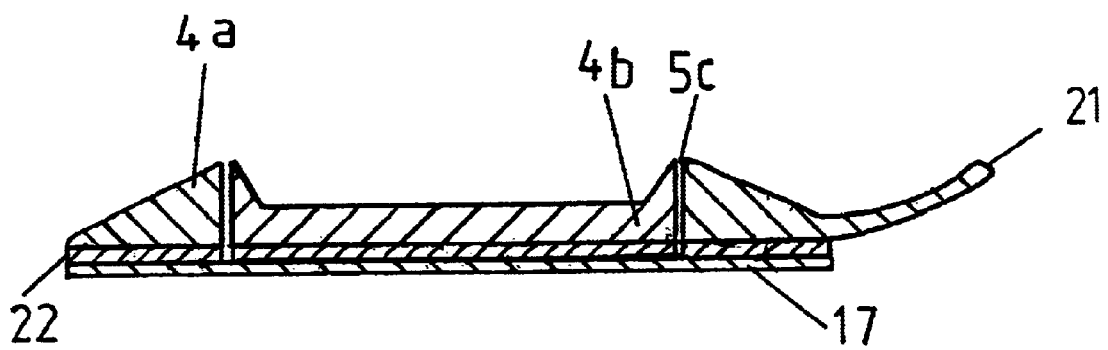

FIG. 16 is a cross section along the line XVI—XVI on FIG. 15.

FIGS. 17 to 20 show various examples of shapes of the periphery line and patches intended to be removed, wherein the shapes are selected for permitting the stitching together of openings left after excision with the least possible remaining deformation and/or scar formation and simultaneously permitting the excision of a patch of substantial breadth in a direction perpendicular or cross-wise to the longitudinal extension of the opening.

Figure 17:
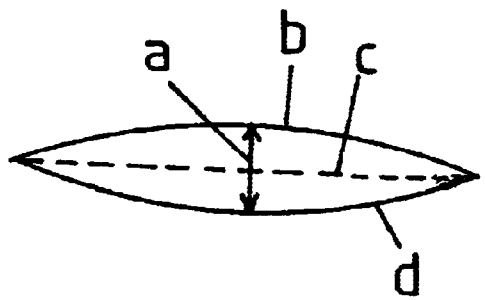

FIG. 17 shows an oval opening, which is preferably shaped with acute edges, such as formed by the intersection of two circle arcs.

Figure 18:
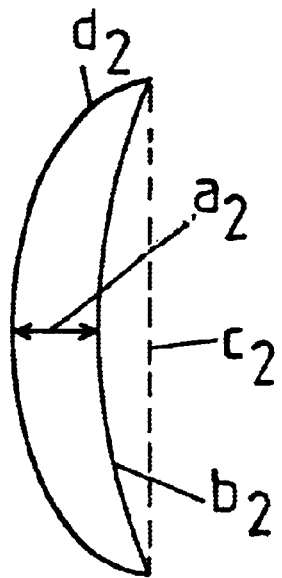

FIG. 18 shows a crescent-shaped opening/patch formed e.g. by two intersecting circle arcs having their centres of curvature on the same side of a line connecting the two intersection points of said arcs.

Figure 19:
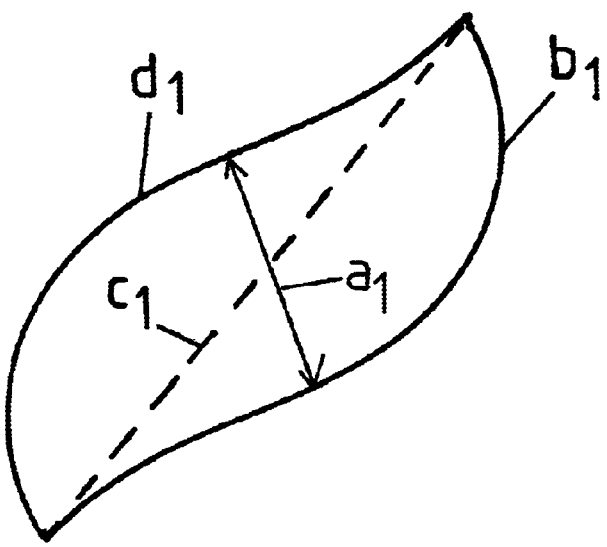

FIG. 19 shows a "deformed" oval in which the two longitudinal sides of the deformed oval show an inflexion point and are similar to lines formed by joining two circle arcs having their centres of curvature on opposite sides of a line c1 connecting the end points of said sides.

Figure 20:
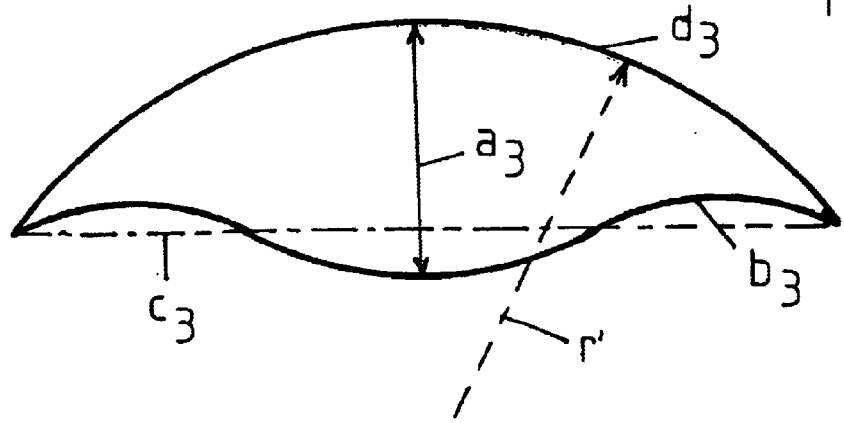

FIG. 20 shows a "deformed crescent" in which one of the sides is formed by three joined parts of circle arcs and where a3 is approximately ½ of the radius r' of the opposite side. The length of each side, respectively, is approximately the same.

Figure 21:
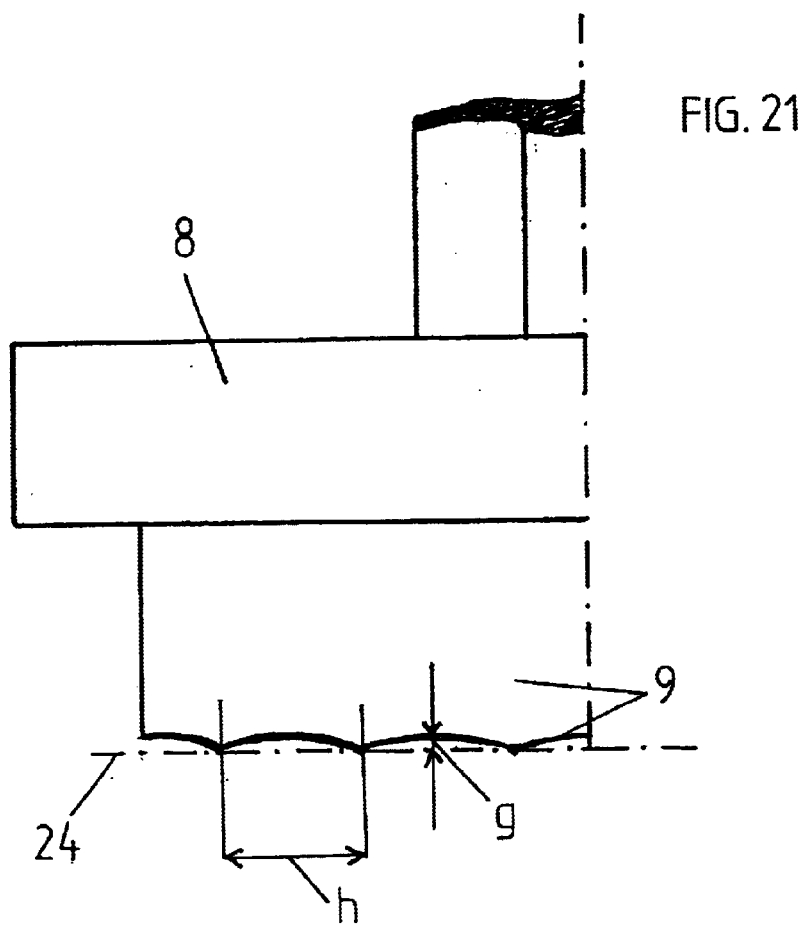

FIG. 21 shows a part of a cutting tool (punch) with a handle 8 and a cutting blade with a cutting edge 9 shaped close to a flat smooth surface indicated with a broken line 24.

A preferred embodiment of this method comprises the application to a substrate 3 of a mask 4a comprising a piece of sheet material having a main opening 7 with a borderline 5a for indicating a periphery line and guiding a cutting, especially punching tool, for making a cut to a desired depth along at least a part of the periphery line. Optionally an array of secondary, minor openings 6 in the mask surround the borderline 5a. The secondary openings preferably have a size which permits the application through the openings of markings on the surface, outside the periphery line, e.g. with a preferably sterilized marking pen, which remain after a removal of the mask. These markings are used to indicate an area adjacent the periphery line, wherein stitches can suitably and evenly be placed for stitching together a preferably resilient substrate layer 3 for closing an opening in said layer formed by excision of a patch 2 of said layer having essentially the shape of the periphery line 1 indicated by the borderline of the mask, The secondary openings are e.g. arranged along a line parallel or commensurate to the inner borderline 5a, e.g. at a distance of at least 1 mm, e.g. about 2 mm and e.g. up to 5 mm therefrom, and preferably with the openings evenly interspaced and of a distance "e" from each other and a distance "d" from the borderline, in a way the positions of stitches give a cosmetically as well as mechanically suitable result.

An adhesive or adhesive coated sheet material used according to this invention, especially a sterilized tape material, should preferably be sufficiently flexible to permit tight adherence to a soft or resilient surface, such as the skin of a mammal, especially the human skin.

The sheet material may consist of only one layer or a composite or laminate of two or more layers, optionally of mutually different characteristics or thickness. Optionally the thickness of the mask can be reduced by removing one or more of the layers of a mask made from a laminate of layers which can be removed one by one without destruction of the mask. A mask of selected thickness can be used for restricting the depth of the cut made by a cutting tool with a stopping means, such as a shoulder, which abuts against and is stopped by the mask.

The thickness of the mask may vary within broad limits, provided that it can be applied to and preferably accommodate to the shape of the substrate, and preferably also perform the various other effects which may be desired, such as guiding a cutting tool. A suitable thickness at or adjacent to the inner borderline 5a of the main opening of the negative mask or the outer borderline 5b of the slab/ "positive mask" 4b, may be e.g. at least 0,5 mm, at least 1 mm or at least 2 mm, and optionally e.g. at most 5 mm or above. The mask may also have a thickness which varies, e.g. a thickness which varies, preferably decreases, from the centre, i.e. the inner borderline 5a, towards the periphery, i.e. the outer borderline 14 of the adhesive part of the mask, either continuously or in steps, e.g. when making the mask from a laminate of layers.

Figure 1:
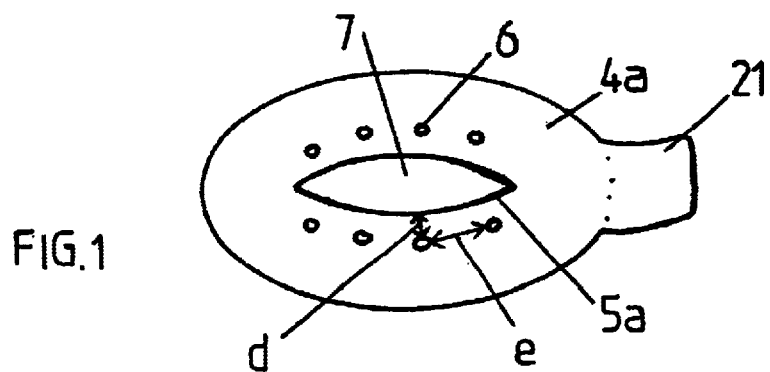
Figure 2:
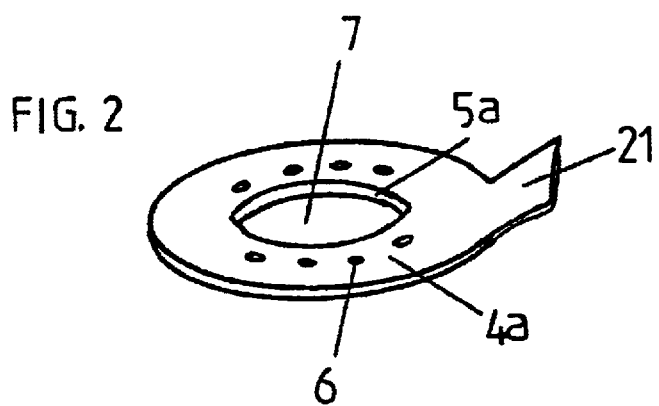
Figure 3:
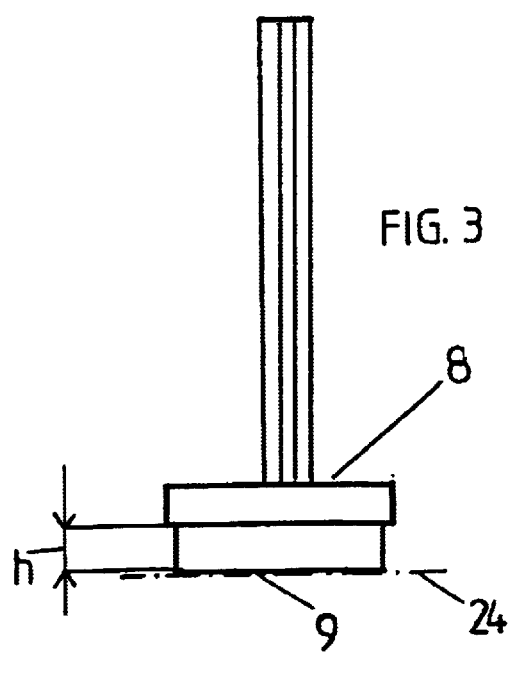
Figure 4:
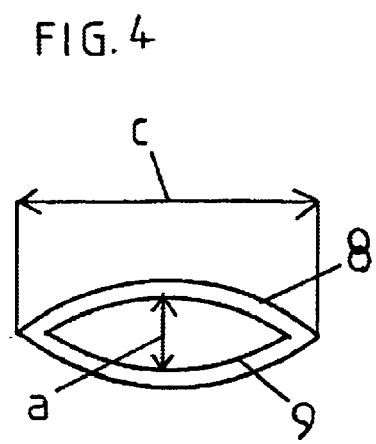
Figure 5:
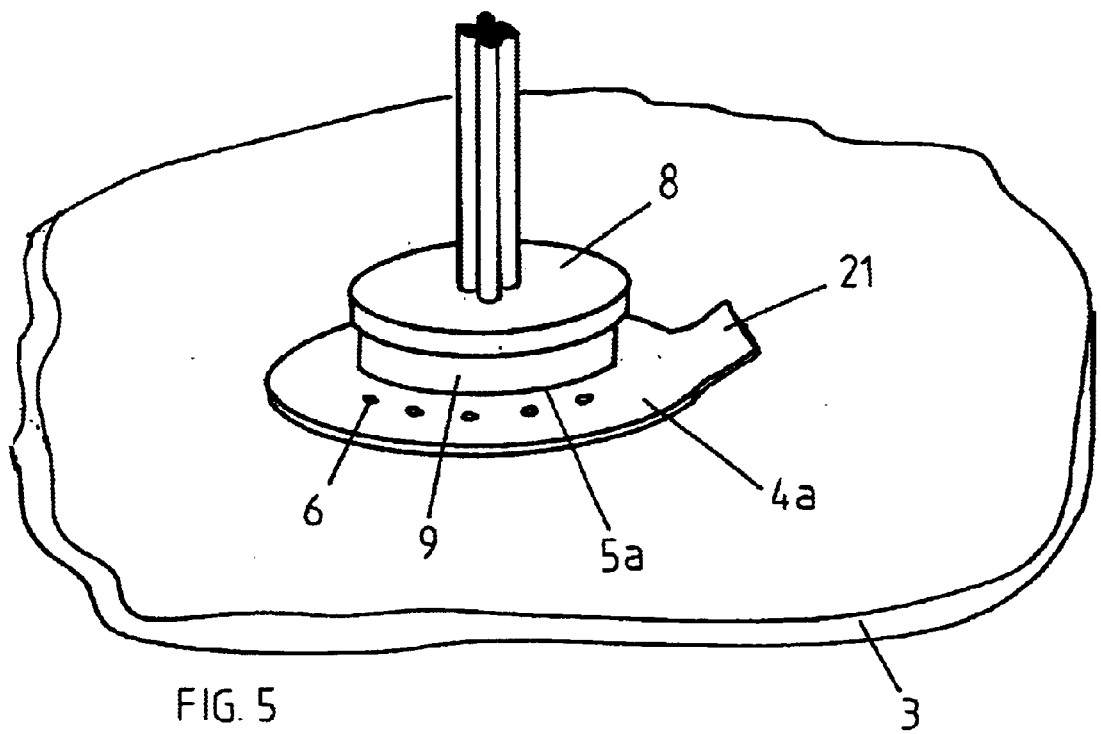
Figure 6:
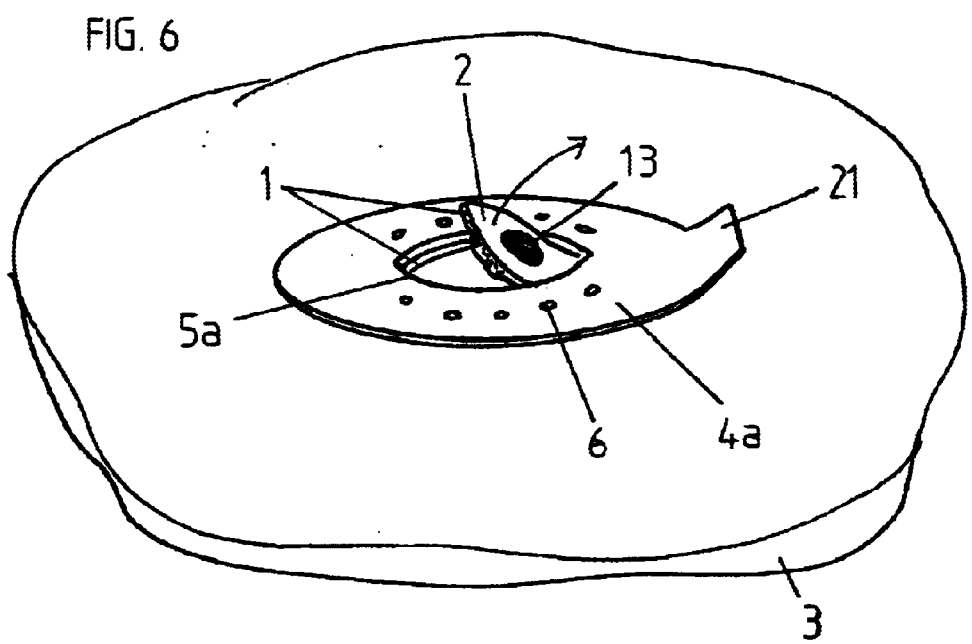

The shape of the mask, such as the main opening 5a is preferably non-circular elongated such as, oval, crescent-shaped, "magnetic-hysteresis-curve-shaped" (such as a "deformed" oval in which the curves forming the opposite sides of the oval have at least one inflexion point) or other shapes, such as circular, which are known to be suitable for stitching together the sides of an excision wound with good healing and/or cosmetic effects. On FIG. 4 a largest extension "c" of the opening is indicated, together with a smallest extension "a" in a therefrom deviating direction, especially in a direction perpendicular or transversal to the direction of c. The ratio of c to a may preferably be above 1.5 or above 2, and may be e.g. up to 3 or above, e.g. up to 5 or above.

Figure 7:
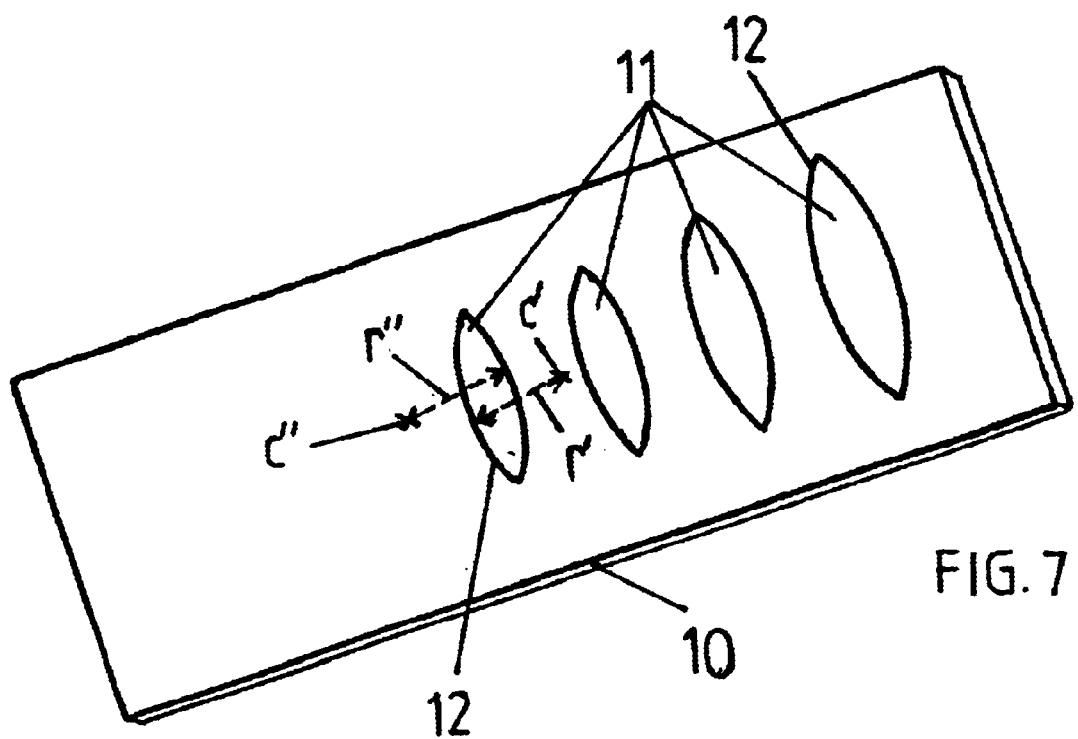
Figure 8:
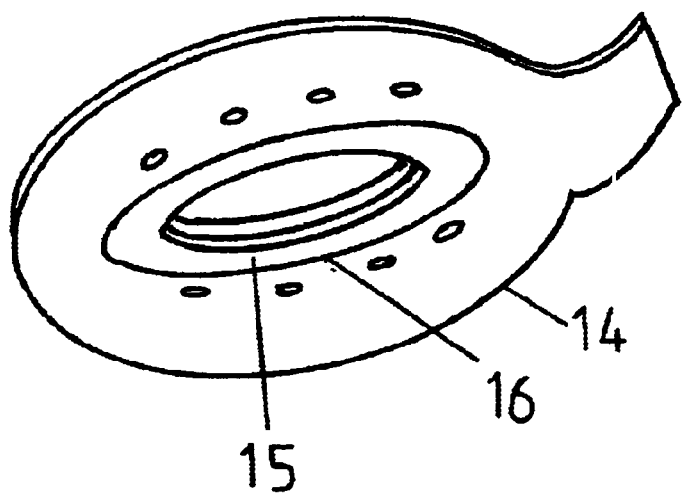
FIG. 8 shows a mask from underneath with a holding space 15 delimited by a holding space limit line 16, for holding e.g. local anaesthetic, growth factors, antibiotics, surface active agents, inflammatory or anti-inflammatory agents in contact with the substrate surface.
Figure 9:
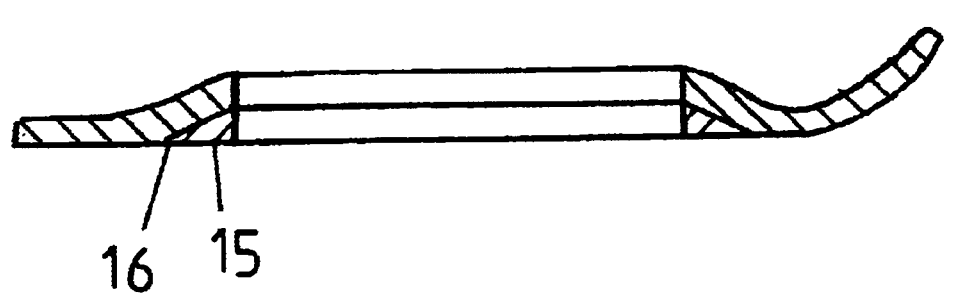
FIGS. 9 and 10 show the mask of FIG. 8 in a cross-section and a view from above, respectively.

The mask borderline 5a, 5b of the main opening or slab, respectively, may e.g. have essentially the shape of two intersecting circle arcs with the centres of the circles on opposite sides of the opening, e.g. as indicated on FIG. 7 for one of the model openings 12 where broken lines r' and r" indicated circle radii from the centres c' and c" respectively. The radii of the two arcs may optionally be essentially of the same size, e.g. with a ratio of up to 2. A crescent-shaped curve can in a similar way be defined as a curve formed by two intersecting circles having their centers on the same side of a straight line between the ends of the crescent.

The masks may also have main openings of other shapes which make it possible to indicate periphery lines 1 of other optionally irregular shapes. Optionally more than one cutting tool may be used to perform an excision of a patch 4 of a substrate layer, e.g. a patch of complicated shape, where two or more cutting tools are used in sequence, guided by and cutting along different parts of the border line of the main opening.

Figure 10:
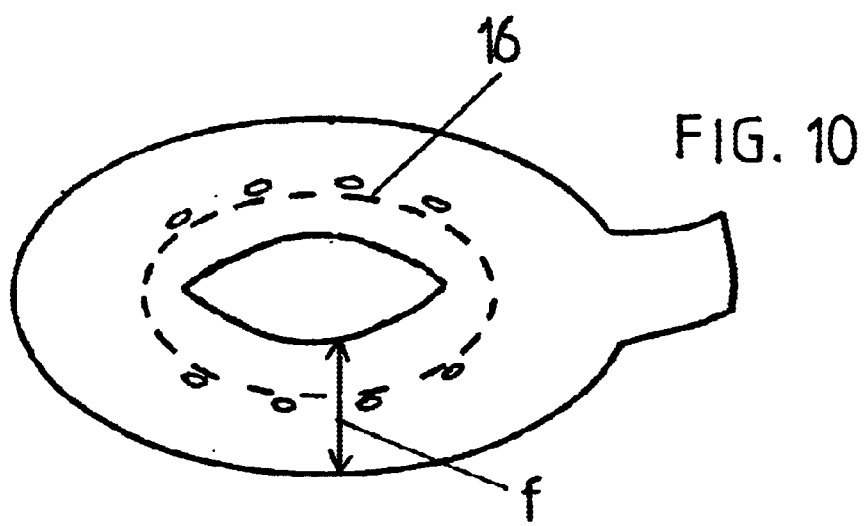

The shape of the periphery, i.e. the outer borderline 14 of the mask may be more or less commensurate to the shape of the inner borderline, i.e. the borderline 5a of the main opening, preferably along the main part of the borderline 5a. The distance between the commensurate parts of the inner and outer borderlines may vary but should normally be sufficient for safe adherence of the mask to the substrate. This distance, indicated with "f" on FIG. 10, may be e.g. at least 3 mm, or at least 5 mm, or at least 10 mm, and optionally e.g. up to 20 mm or up to 50 mm or more.

The mask should preferably exhibit a certain degree of stiffness against deformation in the plane of the sheet material in order to resist or reduce deformations of the original or desired shape of the borderline used for indicating the periphery line before, during or after application of the sheet material on the surface. This stiffness may be improved by such means as increasing the thickness of the sheet material and/or arranging a stiffness enforcing or strengthening element or means adjacent, at or very close to the borderline, along the entire borderline or a part, e.g. mayor part, thereof, e.g. protruding from die surface of the sheet material. This means may also act as a guiding or aiming means for positioning and directing the cutting means or punching and/or cutting element. Preferably, the enforcing means is simultaneously more flexible in directions normal to than in the plane of the sheet material. Optionally the sheet material and/or enforcing means may comprise incisions or cuttings, preferably in a direction essentially normal to the borderline, for improving the flexibility and/or improve adaptation to a curved substrate surface. Optionally the mask or parts thereof may be made from a material, which can be cured, preferably after application on the substrate, for improving its characteristics.

The mask may also be provided with one or more protective or other removable layers, as shown e.g. on FIGS. 11 and 12. Thus a removable layer 17 may be used to protect the sticky or adhesive lower surface of the mask, which is intended to be applied against and adhere to the substrate 3. The mask may also be provided as a "positive and" negative combination mask where the positive mask part 4b is transparent, mobile and thereby removable.

The gripping of the lower and upper layers can be simplified by arranging gripping tabs 18 and 21, which are not provided with an adhesive layer 22 as shown on FIGS. 12 and 14, or are provided with a coating covering the adhesive or sticky surface or layer.

The cutting tool, such as a punching and cutting element, is preferably provided with a cutting edge 9 with essentially the same shape as the borderline 5a, 5b of the sheet material and the periphery line 1 intended to be indicated on the surface of the substrate object, at least after application thereof on the surface, so that the cutting movement of the tool can be guided, aimed and/or directed by a borderline, or part thereof, formed by the border of a main opening 7 or other means on or connected to the sheet material of the mask.

The cutting tool used according to this invention may comprise a cutting edge made from a suitable material, such as metal, e.g. steel or stainless steel, glass, ceramics, plastics and combinations thereof, such as a metal strip bent to the shape of the periphery line and suitably connected to a handle, e.g. made from plastics.

The cutting and/or punching tool is suitably provided with a cutting edge 9 which forms a line, especially an essentially or completely closed loop, preferably a line which along a main part of or along its entire extension is situated in or close to a smooth flat or curved plane indicated with a broken line 24. Preferably the edge deviates, e.g. as indicated on FIG. 21 with "g", at most 5 mm, at most 2 mm, at most 1 mm or at most 0,5 mm from said plane 24 in a direction parallel to the intended cutting direction of the tool, at least along the main part or at least 90 percent of the extension of the edge. Such deviations from a plane or a straight curve, if present, may be substantially regular, e.g. fomring a saw-tooth like or undulating or wave-like pattern, e.g. with a top-to-top distance indicated with "h" on FIG. 21, which may improve the cutting effect and/or improve the grip of the edge at the surface when starting the cut. The distance h may be e.g. at most 5 mm, at most 2 mm or at most 1 mm. The cutting device, especially the cutting blade, is suitably shaped essentially as a cylinder surface or as a part of such a surface, especially at the part thereof which is intended to be supported and guided by the mask, in which case the cutting edge is suitably shaped as the cross section or the main part of the cross section of said cylinder surface with an essentially smooth flat or curved plane, as mentioned above, suitably directed perpendicular to the axis of the cylinder surface. The cutting blade on which the edge is formed may consist e.g. of thin sheet metal, e.g. stainless steel, e.g. with a thickness of at most 2 mm, at most 1 mm or at most 0,5 mm.

The cutting tool or punch according to this invention may be used by hand and may also be combined with various kinds of driving means, such as means which bring the cutting edge to perform a vibrating motion or transfer an impact force to the cutting edge. The driving means is preferably removable from the cutting tool, e.g. for repeated use with throwaway cutting tools. A cutting tool may also be combined with a force exerting means, such as a snap impact means, to a throwaway unit intended to be discarded after use.

Cutting is preferably performed on a skin substrate which is held in a substantially undisturbed or non-stretched condition, e.g. with a stretch elongation of at most 20% or at most 5%, especially in a direction essentially perpendicular to the skin Langer's lines. The cutting motion of a punching tool is usually mainly in a direction essentially perpendicular to the substrate surface, optionally combined with a usually minor movement component in the direction of the substrate surface plane, e.g. at most 20% or at most 10% of the longitudinal extension "c" of the surface patch 2, such as a slight "sawing" motion of the cutting edge, e.g. for cutting through the substrate surface down to a desired depth, e.g. down to the fat tissue under the skin of a human.

The method and devices according to the invention is intended to be used for surgical excision of skin from mammals, especially humans, for cosmetic or other treatments, such as removal of skin tumors. For such purposes it is essential to reach a high grade of accuracy and safety in aiming and cutting, which is achieved with the aid of this invention. Thus, such an excision procedure may comprise the following steps.

1. Identify the skin area to be marked e.g. comprising a skin tumor.
2. Evaluation of the suitable size, shape and position of the surface patch intended to be marked, optionally with a template device comprising one or more periphery line forming means, which can be held at the surface intended to be indicated for excision for simulating a periphery line 1 marking thereon. An optimal size and shape of mask is thereby chosen.

3. After the area for surgery has been cleansed, sterilized, properly draped and anaesthetized the chosen mask comprising of a piece of sheet material is properly applied, which acts as a sterile aiming device, such as a tape with an adhesive layer, comprising a main opening with a borderline 5a (or the application of the transparent "positive" mask 4b) forming a periphery line indicating element of a selected shape and size.

4. In order to guide the coming wound closing suturing an array of marks is optionally applied on the surface through an array of secondary, minor openings 6, surrounding the borderline 5a, preferably with a sterilized pen.

5. A corresponding cutting punch 8 having a cutting edge 9 with the shape of the periphery line guided by the borderline 5a, is positioned in the opening of the mask (alternatively when using a slab/"positive" mask; over the slab 4b), a final control that everything looks correct, followed by the cutting into the surface area layer of the substrate, e.g. through dermis down to subcutaneous fat tissue.

6. The mask is pulled off from the skin.

7. The skin patch is cut off, suitably in the level of the subcutaneous fat tissue and released. If needed, bleeding vessels are coagulated. With the optional aid of the array of skin markings the wound edges are evenly closed by the following stitching operation.

The invention also comprises a piece of sheet material, such as a sterile tape, suited for use in the method according to the invention, which is provided with an adhesive coating on one side which permits the application on and adherence to the skin of mammals, especially humans, for at least a shorter period of time, preferably without causing irritation, wherein the piece of sheet material is shaped with a borderline surrounding a main opening in the sheet material and/or a slab of continuous sheet material, wherein the borderline defines an elongated, essentially oval shape, e.g. formed of two intersecting circle arcs, of which the centres of curvature are situated an opposite sides of the loop formed by said intersecting arcs, the radii of said circles preferably being of essentially the same size.

The sheet material may consist of any of the materials mentioned above or any other suitable material with characteristics which fulfil the requests, also comprising combinations of two or more layers of material having different characteristics. The piece of sheet material (tape) may e.g. at least at the borderline have a thickness of at least 0,5, at least 1 or at least 2 mm, and preferably at most 5 mm.

As mentioned above the invention also comprises a kit for carrying out the method according to the invention and/or including the mask (piece of sheet material) according to the invention, e.g. as disclosed above, and/or a primary and/or secondary template. Such a kit thus may comprise a piece of sheet material with an adhesive coating, such as a sterilized tape, e.g. surgical tape, and a punching/cutting tool with a cutting edge shaped for cutting out a patch of skin of elongated form, wherein the piece of sheet material is provided with a borderline suited for defining an intended periphery line, which borderline surrounds a main opening in and/or a slab of essentially continuous sheet material wherein the periphery line has essentially the shape of the patch of skin intended to be cut out with the punching and cutting tool. The borderline is optionally surrounded by an array of minor, secondary openings. The kit may also comprise a primary and/or secondary template defining the shape of the periphery line as mentioned above.

In this kit at least the punch/cutting tool and the corresponding mask should be sterile, intended for single use and to be packed in a suitable sterile package. The mould/model does not necessarily share the need for single use and sterility.

EXAMPLES

The invention is in the following explained with reference to examples, which are intended only for illustrating the invention without any restriction of the scope thereof.

The cutting and punching tool can be manufacture e.g. with a plastic rod with two oval cutting steel blades inserted in the end of it. The steel blades are put together in such a way that they form an oval; thus a punching/cutting tool.

The mask could be manufactured out of a piece of flat flexible plastics e.g. PVC-plastics, approximately 1 mm in thickness and with one adhesive side. The oval hole in the center of the mask is cut out by a manufacturing tool, resulting in a hole/defect that perfectly fit it's corresponding punch/cutting tool. The secondary holes/minor openings can be drilled or punched out.

The template can be made from a sheet of plastic, e.g. 1 mm thick and preferably non-transparent.

Using irradiation or e.g. ethylene oxide it is possible to perform the sterilization of the in going components of the kit.

Clinical Example 1

A male person 67 years of age, with a circular shaped naevus (localized skin disorder) on his lower chest was referred from his family doctor to the outpatient surgical ward. The naevus had over the last months become more and more irritating and it had also once been bleeding. The size of the naevus was approximately 3×4 mm.

A history like this might correspond to an early malignant transformation of an initially benign naevus. Great care must therefor be taken to ensure sufficient free margins when performing the following surgery.

With the template device a suitable size and form of the punch and mask set was chosen; an oval shaped with a 9×27mm main opening. The area of the naevus was cleansed, sterilized and properly draped. Local anesthetics was administered. The chosen mask was adhered in a proper way to the dried and sterilized area, leaving the main opening with equal free and even margins, respectively, surrounding the naevus. The underlaying skin of the secondary minor openings was marked with a sterile pen. The corresponding cutting punch was then positioned in the main opening, a final control that everything looked good, followed by the actual cut-through procedure into the designated skin area down to the subcutaneous fat tissue. The mask was then pulled of the skin. The punched out skin patch including the naevus was then taken away, with the aid of a surgical knife. The skin patch was sent for microscopy analysis.

Guided by the marks from the secondary minor openings, the skin edges of the wound were evenly sutured (or in other way permanent adapted) to each other.

Clinical Example 2

A woman, 22 years of age, referred from a general practitioner due to a rounded unaesthetic scar formation on her left thigh of approximately 4×4 mm in size. Due to her history, the finding was classified being as likely of benign origin.

With the template device a suitable size and form of the punch and mask set was chosen; an oval shaped with a 5×15 mm main opening. The area of the scar formation was cleansed, sterilized and properly draped. Local anaesthetics was administered. The chosen mask was adhered in a proper way to the dried and sterilized area, leaving the main opening with equal force and even margins, respectively, surrounding the scar formation. The under laying skin of the secondary minor openings was marked with a sterile pen. The corresponding cutting punch was then positioned in the main opening, a final control that everything looked good, followed by the actual cut through procedure into designated skin area down to the subcutaneous fat tissue. The mask was then pulled of the skin. The punched out skin patch including the scar formation was then taken away, with the aid of a surgical knife. The skin patch was sent for microscopy analysis. Guided by the marks from the secondary minor openings the skin edges of the wound were evenly sutured to each other.

What is claimed is:

1. A method for indicating a periphery line of a patch of skin of elongated shape of a mammal and removing said patch of skin, which comprises applying onto the skin an adhesive mask of a sheet material, which is flexible to permit tight adherence to the skin, said mask comprising a main opening with a borderline with the shape of the patch of skin intended to be removed, said mask having an adhesive surface which when applied against the skin makes the mask adhere to the skin, and fitting into the main opening of the mask a cutting punch with a cutting edge with the shape of said periphery line and with a tight fit to said opening, so that the cutting punch is mechanically guided and directed by the mask, and applying a force onto the cutting punch for cutting through dermis, and removing the patch of skin from the mammal.

2. A method according to claim 1, wherein the mammal is a human.

3. A method according to claim 2, wherein the mask is provided with an array of secondary, minor openings arranged evenly spaced around the main opening, and applying through said secondary openings marks onto the skin which indicate an area adjacent the periphery line where stitches can suitably be placed for closing an opening in the skin formed by removing the patch of skin.

4. A method according to claim 2, which comprises indicating and removing a patch of skin with pathologic defects.

5. A method according to claim 2, which comprises indicating and removing a patch of skin of oval shape with a ratio of lengthwise extension to transverse extension of at least 1.5.

6. A kit suited for carrying out the method according to claim 1 for indicating a periphery line of a patch of skin of elongated shape of a mammal and removing said patch of skin, which comprises I) aN adhesive mask of a sheet material, which is flexible to permit tight adherence to the skin, comprising a main opening of elongated shape with a borderline with the shape of the patch of skin intended to be removed, said mask having an adhesive surface, which surface when applied against the skin makes the mask adhere to the skin, and II) a cutting punch with a cutting edge having the shape of the borderline of the main opening of the mask and fitting with a tight fit into said main opening, so that the cutting punch can be mechanically guided and directed by the borderline of the main opening of the mask.

7. A kit according to claim 6 which in addition to the adhesive mask and the cutting punch also comprises a template device of a sheet material with an opening suited to be held close to the skin intended to be indicated for excision for simulating a periphery line marking thereon with the mask.

8. A kit according to claim 7 wherein the main opening in the mask and the cutting edge of the cutting punch are of oval shape with a ratio of lengthwise extension to transverse extension of at least 1.5.

9. A kit according to claim 6, wherein the cutting punch is provided with a cutting blade shaped as a cylinder surface at the part thereof which is intended to be mechanically guided by the mask.

10. A kit according to claim 6, wherein the cutting punch has a cutting edge which along a main part of its extension deviates at most 1 mm from a smooth plane.

11. A mask suited for carrying out the method according to claim 2 consisting of a piece of sheet material with an elongated opening with a border line and an adhesive surface which when applied against the skin of a human makes the mask adhere to the skin, said mask being flexible to permit tight adherence to the skin, said mask being provided with means acting as guiding and directing means for mechanically guiding a skin cutting punch with a cutting edge with the shape of said border line and with a tight fit to said main opening.

12. A mask according to claim 11, which mask is provided with an array of secondary, minor openings suited for inserting a marking pen for making a mark on the skin, arranged evenly spaced around the main opening at a distance of up to 5 mm from the main opening.

* * * * *